United States Patent [19]
Mandel et al.

[11] Patent Number: 5,631,022
[45] Date of Patent: May 20, 1997

[54] PICOSULFATE DOSAGE FORM

[75] Inventors: Kenneth G. Mandel, Fairfield; Paula D. Davis, Cincinnati, both of Ohio

[73] Assignee: The Procter & Gamble Company, Cincinnati, Ohio

[21] Appl. No.: 498,612

[22] Filed: Jul. 6, 1995

Related U.S. Application Data

[63] Continuation of Ser. No. 139,364, Oct. 19, 1993, abandoned.

[51] Int. Cl.$^6$ ....................................... A61K 9/64
[52] U.S. Cl. ........................... 424/456; 424/451; 424/464; 514/892
[58] Field of Search .................... 424/456, 457, 424/464; 514/892

[56] References Cited

U.S. PATENT DOCUMENTS

| | | | |
|---|---|---|---|
| 2,870,061 | 1/1959 | Huggins | 167/56 |
| 3,080,286 | 3/1963 | Neary | 167/56 |
| 4,369,172 | 1/1983 | Schor | 424/19 |
| 4,690,816 | 9/1987 | Hata et al. | 424/456 |
| 4,948,591 | 8/1990 | Yamada | 424/456 |
| 5,068,110 | 11/1991 | Fawzi | 424/461 |
| 5,194,464 | 3/1993 | Itoh | 524/42 |

FOREIGN PATENT DOCUMENTS

| | | | |
|---|---|---|---|
| 0341584 | 11/1989 | European Pat. Off. | A61K 31/44 |
| 57-31864 | 2/1982 | Japan | A61J 3/07 |
| 1009932 | 1/1989 | Japan | A61K 9/48 |
| 1-258619 | 10/1989 | Japan | A61K 31/44 |
| 1-254626 | 10/1989 | Japan | A61K 31/44 |
| 2-188524 | 7/1990 | Japan | A61K 31/44 |
| 4066531 | 3/1992 | Japan | A61K 9/48 |
| 2230442 | 10/1990 | United Kingdom | A61J 3/07 |
| 2230441 | 10/1990 | United Kingdom | A61J 3/07 |
| 91/12795 | 9/1991 | WIPO | A61K 9/22 |

OTHER PUBLICATIONS

Hillestad, B., R. B. Sund, and M. Buajordet "Intestinal Handling of Bisacodyl and Picosulphate by Everted Sacs of the Rat Jejunum and Stripped Colon", Acta pharmacol. el toxicol., vol. 51 (1982), pp. 388–394.

Jauch, R., R. Hankewitz, K. Beschke, and H. Pelzer "Bis–(p-hydroxyphenyl)–pyridyl–2–methane: The Common Laxative Principle of Bisacodyl and Sodium Picosulfate", Arzneim.–Forsch. (Drug Res.), vol. 25 (1975), No. 11, pp. 1796–1800.

Pala, G., G. Coppi and E. Crescenzi "On the Laxative Properteis of Sulfuric Esters of Phenols, with Particular Reference to 4,4'–(2–picolylidene)–bis–phenylsulfuric Acid Disodium Salt (Picosulfol)", Arch. int. Pharmacodyn., vol. 164 (1966), No. 2, pp. 356–369.

Sund, R. B., K. Songedal, T. Harestad, B. Salvesen, and S. Kristiansen "Enterohepatic Circulation, Urinary Excretion and Laxative Action of Some Bisacodyl Derivatives after Intragastric Administration in the Rat" Acta pharmacol. et toxicol., vol. 48 (1981), pp. 73–80.

Sund, R. B. "Aspects of the Pharmacology of Diphenylmethane Laxatives (Bisacodyl, Oxphenisatin and Phenolphthalein derivatives)", Nor. Pharm. Acta, vol. 45 (1983), pp. 125–162.

Primary Examiner—D. Gabrielle Phelan
Attorney, Agent, or Firm—Betty J. Zea; Jean R. Crosmun; David L. Suter

[57] ABSTRACT

A pharmaceutical laxative composition in unit dosage form, for peroral administration of picosulphate to a human or other animal subject, comprising a safe and effective amount of picosulphate in a rapidly dissolving matrix; and a proximal colonic delivery carrier which effects release of said picosulphate substantially near the junction between the small intestine and the colon or within the colon of said subject. This invention also involves methods for providing laxation for humans and other animals in need thereof by peroral administration of such compositions.

13 Claims, No Drawings

PICOSULFATE DOSAGE FORM

This is a continuation of application Ser. No. 08/139,364, filed on Oct. 19, 1993, now abandoned.

TECHNICAL FIELD

This invention involves a novel dosage form of picosulphate for providing laxation in the colon.

BACKGROUND OF THE INVENTION

Picosulphate, 4,4'-(2-pyridylmethylene)-bisphenol-bis (hydrogen sulfate) (ester) disodium salt, is disclosed in the *Merck Index*, 11th ed. (1989), S. Budavari, ed., No. 7377, p.1175. Picosulphate is a known active ingredient for use as a laxative. Picosulphate is an inactive prodrug that is hydrolyzed by colonic bacteria to bis-(p-hydroxyphenyl)-pyridyl-2-methane (commonly known as "desacetyl bisacodyl") which is the active species). Contact of the desacetyl bisacodyl with the mucosa stimulates sensory nerve endings to produce increased propulsive peristaltic contractions of the colon which accelerate movement of contents through the colon. Administration of picosulphate has also been shown to promote fluid and ion accumulation in the colon, which increases its laxative effect. Since desacetyl bisacodyl acts upon contact with lumenal mucosa of the large intestine, its laxative effect is dependent upon generation of sufficient levels of the drug in the lumen of the colon.

Commercially available picosulphate laxatives are designed to deliver the picosulphate to the small intestine. Although these dose forms provide effective laxative activity, doses which produce maximal laxation also evoke undesirable side effects such as secondary episodes of diarrhea or repeat bowel movements.

It has been surprisingly discovered that delivery of picosulphate to the colon as a rapidly dissolving matrix, or in a solubilized form, produces maximal laxation at doses which do not evoke secondary episodes of diarrhea.

An advantage of providing picosulphate to patients using the compositions of this invention is that laxation benefits are generally achieved without the secondary diarrhea commonly associated with conventional picosulphate compositions. Another advantage is that such laxation benefits are often achieved more quickly than with conventional picosulphate compositions. Another advantage is that a lesser dosage amount of picosulphate is needed to achieve laxation than is needed with conventional picosulphate compositions. Another advantage is that due to the lesser dosage amount and the more prompt onset of laxation activity, the side effects of cramping and pain are lessened.

SUMMARY OF THE INVENTION

A pharmaceutical laxative composition in unit dosage form, for peroral administration of picosulphate to a human or other animal subject, comprising a safe and effective amount of picosulphate in a rapidly dissolving matrix; and a proximal colonic delivery carrier which effects release of said picosulphate near the junction between the small intestine and the colon or within the colon.

This invention also involves methods for providing laxation for humans and other animals in need thereof by peroral administration of such compositions.

DETAILED DESCRIPTION OF THE INVENTION

This invention involves pharmaceutical compositions in unit dosage form, for peroral administration of picosulphate to a human or other animal subject, comprising (a) a safe and effective amount of rapidly dissolving picosulphate matrix; and (b) a proximal colonic delivery carrier which effects release of said picosulphate substantially near the junction between the small intestine and the colon or within the colon. As used herein, "near the junction between the small intestine and the colon"0 means within the intestinal tract close to but on either side of the the juncture joining the small intestine with the large intestine; this also includes release within the proximal colon. As used herein, "colon" refers to the portion of the large intestine which extends from the juncture with the small intestine up to but not including the rectum. The picosulphate may be released near the junction between the small intestine and the colon, within the transverse colon, or within the descending colon. Preferably the picosulphate is released substantially near the junction between the small intestine and the colon.

The methods and compositions of this invention utilize a safe and effective amount of picosulphate. The term "safe and effective amount", as used herein, means an amount of picosulphate high enough to provide a significant positive modification of the condition to be treated, but low enough to avoid serious side effects (at a reasonable benefit/risk ratio), within the scope of sound medical judgment. A safe and effective amount of picosulphate will vary with the particular condition being treated, the age and physical condition of the patient being treated, the severity of the condition, the duration of the treatment, the nature of concurrent therapy and like factors. An effective dose of picosulphate in compositions of this invention is preferably substantially lower than the dose of picosulphate required to achieve efficacy with conventional picosulphate-containing compositions.

A safe and effective dose of picosulphate in a composition of this invention preferably provides from about 0.1 mg to about 25 mg of picosulphate locally to the lumen of the lower gastrointestinal tract near the junction between the small intestine and the colon or within the colon of a human patient. A preferred amount of picosulphate dosed to a human patient is from about 0.5 mg to about 15 mg; more preferred is from about 1 mg to about 10 mg; more preferred still is from about 1 mg to about 3 mg. A unit dosage form of this invention preferably contains a single dose of picosulphate in the above amounts. Generally, no more than about 50 mg picosulphate should be ingested by a single patient in any given day.

It is desirable to minimize colonic absorption of desacetyl bisacodyl from the original peroral dose of picosulphate while achieving therapeutically effective levels of the drug in the lumen of the colon.

As used herein, "rapidly dissolve" means dissolve substantially completely within from about 1 minute to about 20 minutes once dissolution commences.

A dosage form of this invention comprises two functional parts: (1) a picosulphate matrix; and (2) a proximal colonic delivery carrier which delays release of the picosulphate until the dosage form has been transported through the upper gastrointestinal tract to a point near the junction of the small intestine and colon or within the colon.

Picosulphate Matrix

As used herein, "picosulphate matrix" comprises picosulphate in a physical form or composition from which picosulphate rapidly dissolves in the intestinal juices. This preferably consists of a solution of picosulphate or solid picosulphate having a mean particle size below about 100 µm.

A preferred picosulphate matrix is comprised of a solid dispersion of picosulphate in a water-soluble carrier such as polyethylene glycol (molecular weight greater than about 1000 daltons), poloxamer, citric acid, tartaric acid, dextrose monohydrate, or urea. Typical ratios (weight:weight) of water-soluble carrier to picosulphate range from about 1:1 to about 20:1. The solid dispersions may be prepared by a number of techniques well known to those skilled in the art, such as solvent evaporation, melt, spray drying, or freeze drying. The solvent evaporation technique involves dissolution of both the water-soluble carrier and picosulphate in a volatile solvent which is then removed by evaporation or spray drying. The melt technique involves preparation of a melt of the water-soluble carrier and picosulphate followed by solidification to produce a solid which may then be granulated. Aqueous or aqueous/water miscible solvent solutions of the water-soluble carrier and picosulphate may also be prepared and either spray dried or lyophilized to produce a solid dispersion. Preferred water-soluble carriers are those which are also solvents for picosulphate, such as polyethylene glycol. Such solid dispersions are preferably incorporated into the unit dosage form as solid particulates, preferably less than about 1 mm in diameter.

Another preferred picosulphate matrix is comprised of a solution of picosulphate in a water-miscible, pharmaceutically-acceptable solvent that is liquid at body temperature (about 37° C.). A preferred solvent for such solutions is polyethylene glycol (molecular weight less than about 1000 daltons). The amount of picosulphate present in such solution will be a function of the particular solvent, but concentrations typically range from about 0.5% to about 30%, preferably from about 1% to about 20%, more preferably from about 5% to about 15%. For purposes of this invention, a useful description of how to incorporate solutions of picosulphate into conventional dosage forms is has been described in Japanese Pat. Publication #Hei 1-258619, of M. Takahashi, "New sodium picosulphate agent showing rapid dispersion in the intestine".

The picosulphate matrix can comprise, in addition to the preceding rapidly-dissolving or solubilized preparations of picosulphate, excipients which improve the performance of the picosulphate matrix. Such additional components may include, for example, dispersants which help disperse the picosulphate in the gastrointestinal juices to aid in the rapid dissolution of the picosulphate. Other optional components include preservatives, stabilizers, materials for facilitating the manufacture of the dosage form, and other excipients.

The picosulphate matrix may comprise a powder of picosulphate, or granulated solid dispersion that is encapsulated in a hard gelatin capsule that is subsequently coated with the proximal colonic delivery carrier. The picosulphate powder composition may also include various excipients such as diluents (e.g., lactose, sucrose, starch, calcium sulfate, dicalcium phosphate, microcrystalline cellulose); binders (e.g., polyvinylpyrrolidone, pregelatinized starch, gelatin, hydroxypropyl methylcellulose, methylcellulose, hydroxyethyl cellulose, hydroxypropyl cellulose); lubricants (e.g., stearic acid, magnesium stearate); disintegrants (e.g., sodium starch glycolate, cross-linked polyvinylpyrrolidone, cross-linked carboxymethyl cellulose); glidants (e.g., fumed silica); and buffers. The powder mixture may be prepared via a number of techniques well-known to pharmaceutical science such as dry mixing, wet granulation, and fluid bed granulation. The solids mixture may be prepared via a number of techniques well-known to pharmaceutical science such as dry mixing, wet granulation, and fluid bed granulation, and be filled into capsules or compressed into tablets using conventional equipment and processes. Any compressed tablet preferably is made such that it rapidly disintegrates in intestinal juices. The picosulphate matrix may comprise a solid dispersion of picosulphate and a water-soluble carrier that is filled as a melt into hard or soft elastic gelatin (SEG) capsules that are subsequently coated with the proximal colonic delivery carrier. The picosulphate matrix may comprise a compressed picosulphate tablet. The compressed tablet preferably is made such that it rapidly disintegrates in intestinal juices. It may include any of the excipients listed for powder compositions above. Said tablets are subsequently coated with the proximal colonic delivery carrier.

Proximal Colonic Delivery Carrier

In the compositions of this invention, the proximal colonic delivery carrier prevents the release of picosulphate as the dosage form passes through the upper gastrointestinal tract, including the mouth, esophagus, stomach, and small intestine, until the dosage form is near the junction between the small intestine and the colon or is in the colon.

As used herein, "proximal colonic delivery carrier", is a material or materials which encases the picosulphate matrix in a manner that provides a dosage form for peroral ingestion. As such, the proximal colonic delivery carrier can consist of coating technologies encasing conventional tablets or capsules, specifically designed shells of capsules, or of other technologies which will prevent release and lumenal exposure of picosulphate as the dosage form passes through the upper regions of the GI tract.

Enteric Coatings.

Three types of proximal colonic delivery carriers are preferred. The first is a coating or covering applied to conventional dosage forms comprising the picosulphate matrix such as compressed tablets, hard gelatin capsules, and soft elastic gelatin capsules. Suitable coating materials include pH-sensitive (enteric) materials, which remain intact in the lower pH environs of the stomach and small intestine, but which disintegrate or dissolve at the pH commonly found in the latter portion of the small intestine or beginning of the colon of the patient.

Preferred enteric coating materials useful for preparing proximal colonic delivery carrier for the unit dosage form compositions of this invention include pH-sensitive polymers which do not dissolve in the lower pH environs of the stomach and the upper portions of the small intestine (pHs lower than about 6.5), but which disintegrate or dissolve at the pH commonly found in the latter portions of the small intestine or in the proximal region of the colon, e.g., above pH 6.5. Such polymers include polymethacrylates (e.g., Eudragit® Type S, or combinations of Eudragit® Types L and S, Röhm Pharma GmbH, Darmstadt, Germany), hydroxypropyl methylcellulose phthalate, shellac, and polyvinyl acetate phthalate. The pH at which such pH-sensitive polymers begin to dissolve and the thickness of coating will determine the site in the intestinal lumen at which the picosulphate matrix is released. Typically, higher pH dissolution points and increased amounts of pH-sensitive polymer will increase the distance the unit dosage form will travel in the small intestine and colon prior to release of the picosulphate. For certain compositions of this invention, preferred pH-sensitive enteric materials dissolve only at a pH of greater than about 6.5, more preferred enteric materials dissolve only at pH of greater than about 6.8; also preferred are enteric materials which dissolve only at a pH of greater than about 7. An especially preferred pH-sensitive material is a polymethacrylate polymer (Eudragit® S) with a pH dissolution value of about pH 7.

Time-dependent release Materials

The second preferred proximal colonic delivery carrier is prepared by coating a conventional tablet, hard gelatin capsule, or soft gelatin capsule incorporating the picosulphate matrix with a time-dependent release material which remains intact in the lower pH environs of the stomach, but dissolves slowly as the dosage forms passes through the small intestine, followed by a coating of an enteric material which dissolves/disperses when the dosage form enters the upper small intestine (duodenum). The enteric outer coating layer primarily prevents initiation of dissolution/dispersion of the underlying time-dependent release coating within the stomach. The time-dependent material further delays the release of the picosulphate matrix until the dosage form reaches a point near the junction of the small intestine and colon, or within the colon, based upon its dissolution rate and thickness and the intestinal transit rate.

Suitable coatings can also be made of materials which are affected little by changes in pH, but which dissolve or erode slowly as the dosage form passes through the gastrointestinal tract; the thickness of covering is selected such that the covering is breeched, releasing the picosulphate matrix, after the time required for the dosage form to travel approximately to the colon. The delivery time can be predetermined based on environmental factors affecting its dissolution and the thickness of the enteric layer. Additionally, suitable coatings can be made of materials that permit water diffusion, but not drug diffusion. These coatings permit hydration and swelling of the contents of the tablet or capsule which then releases the drug matrix a given time following exposure of the coated tablet or capsule to the fluids of the gastrointestinal tract. Coatings made from materials or mixtures of materials which combine aspects of the pH-release and time-dependent release mechanisms described below are also suitable.

Technologies suitable for achieving the desired results, such as those described in the two preceding paragraphs, are described by Klaus Lehmann, PRACTICAL COURSE IN LACQUER COATING, Röhm Pharma GmbH, Weiterstadt Germany (1989); and in Eudragit® Technical Data Sheets published by R öhm Pharma GmbH (1991 ), both incorporated herein by reference.

Preferred time-dependent release coating materials include cellulosic derivatives, such as methyl cellulose, carboxymethyl cellulose, hydroxyethyl cellulose, hydroxypropyl cellulose,,and hydroxypropyl methylcellulose. The dissolution rate of these and other time-dependent release materials is largely pH independent and will be a function of molecular weight and degree of substituent substitution. The thickness of the layer of timed-release material, coating conditions, and type and level of coating aids may also influence the rate of dissolution. The rate of dissolution of the time-dependent release material in combination with the intestinal transit rate of the dosage form will control the site in the intestinal lumen at which the picosulphate matrix is released.

Preferred enteric coating materials suitable for compositions of the preceding paragraph include pH-sensitive polymers, such as polymethacrylates (e.g., Eudragit Types L and L-55, Röhm Pharma, Darmstadt, Germany), cellulose acetate phthalate, hydroxypropyl methylcellulose phthalate, and polyvinyl acetate phthalate, which are insoluble at the pH of the gastric environment, but will dissolve at various pH's above about pH 5 and less than about 6.5. The purpose of the enteric coating of these compositions is to delay the start of dissolution/erosion of the time-dependent release coating until the dosage form has emptied from the stomach.

Coating aids such as plasticizers and talc may be incorporated into the both sorts of coating compositions—both pH-sensitive enteric coatings and time-dependent release coatings. Compressed tablets, and soft and hard gelatin capsules are typically coated in fluidized bed equipment. Tablets and capsules are also typically coated in perforated pans. Tablets may also be coated via compression coating.

Pulse Capsules

The third preferred proximal colonic delivery carrier of this invention is a pulse capsule, such as Pulsincap®. As used herein, "pulse capsules" include capsules described in U.K. Patent Application Nos. 2,230,441A and 5 2,230,442A of National Research Development Corporation, published October 24, 1990; and PCT Patent Application No. WO 91/12795 of National Research Corporation, published Sept. 5, 1991, all of which have U.S. patent application equivalents and are incorporated herein by reference. One form of such a capsule is Pulsincap® manufactured by Scherer DDS, Clydesbanke, Scotland, U.K.

Preferred pulse capsules comprise a water-insoluble male capsule shell, a water-dispersible or swellable hydrophilic plug, and a water-soluble female capsule shell. The male and female shells preferably have the size, shape, and fit of conventional hard gelatin capsule male and female mating shells.

For preferred pulse capsule unit dosage form compositions of this invention, the picosulphate matrix is contained in the male capsule shell and enclosed with the hydrophilic plug such that the hydrophilic plug blocks the entire opening of the male shell. The female shell covers the exposed portion of the plug and extends along the outer cylindrical surface of the male shell.

In contact with the fluids of the stomach and the intestines beyond, the female shell of a pulse capsule dissolves and the hydrophilic plug hydrates. The composition and size of the hydrophilic plug is selected such that the hydrophilic plug disengages from the male capsule shell after a predetermined amount of time, releasing the picosulphate matrix at the approximate time when the dosage form reaches the colon.

A preferred pulse capsule proximal colonic delivery carrier additionally comprises a pH sensitive material that dissolves at a pH typically associated with the upper small intestine (duodenum). This coating encompasses the capsule such that the female capsule shell does not dissolve, and hydration of the hydrophilic plug does not begin until the unit dosage form has emptied from the stomach. This controlled delay eliminates variability due to differences in gastric emptying time (time between ingestion of the unit dosage form and its being emptied from the stomach) when determining the amount of time desired between dissolution of the female shell and disengagement of the plug from the male shell opening.

A preferred composition of the present invention includes a picosulphate matrix incorporated into a Pulsincap® capsule onto which an enteric coating of the type described in the preceding paragraph is applied.

Optional Ingredients

The compositions of this inventions can optionally include active drug ingredients in addition to picosulphate. Non-limiting examples of other active drug agents and amounts typically present in such compositions include the following: ducosate sodium, calcium or potassium, from about 5 mg to about 500 mg, preferably from about 50 mg to about 250 mg; glycyrrhiza extract comprising from about 5% to about 30%, preferably from about 10% to about 16%, glycyrrhizic acid, from about 2 mg to about 200 mg, preferably from about 20 mg to about 100 mg.

Methods

Another aspect of this invention is methods for providing laxation for hu- mans and animals in need thereof by peroral administration of the above-described compositions. Conditions for which such laxation may beneficially be provided include the following: constipation, adjunctive therapy for constipation associated with irritable bowel syndrome, and bowel cleansing prior to diagnostic or surgical procedures.

Dosages of the compositions of this invention described herein above are preferably administered when laxation is needed. One dose is often sufficient to provide the needed laxation, but several dosages can be used sequentially when needed. Such sequential doses are preferably provided to a patient from about 8 hours to about 24 hours apart, up to a maximum of about 4 such dosages. Typically, a single dose of picosulphate invokes laxation.

EXAMPLES

The following non-limiting examples provide typical formulations for compositions of this invention, and typical methods for treating human disorders with such compositions.

| Picosulphate Matrix | | Proximal Colonic Delivery Carrier | |
|---|---|---|---|
| Component | mg/unit dose | Component | mg/unit dose |
| Picosulphate | 5.0 | Polymethacrylates | 8.7 |
| Lactose | 0.5 | (Eudragit S-100) | |
| Dextrates | 25.0 | Dibutyl Phthalate | 1.7 |
| Crospovidone | 5.0 | Talcum | 2.3 |
| Croscarmellose | 5.0 | Ferric Oxide | 1.3 |
| Pregelatinized Starch | 15.0 | | |
| Microcrystalline cellulose | 48.1 | | |
| Magnesium Stearate | 0.4 | | |

Picosulphate Matrix

Picosulphate is mixed with dextrates followed by addition of a preblended mixture of microcrystalline cellulose, crospovidone, croscarmellose, pregelatinized starch, and fumed silica. Magnesium stearate is then added to the mixture with additional mixing. The resulting powder blend is compressed into tablets.

Proximal Colonic Delivery Carrier

Eudragit S-100 and dibutyl phthalate are dissolved into 85 pads isopropyl alcohol. Talcum and ferric oxide are subsequently added to the solution followed by homogenization. The resulting suspension is then applied to the compressed tablets of the picosulphate matrix using a perforated pan coater.

Method

A person swallows 1 tablet and experiences a single episode of laxation hours later without excess laxative-induced cramping.

Example 2

| Picosulphate Matrix | | Proximal Colonic Delivery Carrier | |
|---|---|---|---|
| Component | mg/unit dose | Component | mg/unit dose |
| Picosulphate | 5.0 | Polymethacrylates | 8.7 |
| Lactose | 0.2 | (Eudragit S-100) | |
| Dextrates | 25.0 | Dibutyl Phthalate | 1.7 |
| | | Talcum | 2.3 |
| | | Ferric Oxide | 1.3 |

Picosulphate Matrix

Picosulphate is blended with dextrates and filled into a hard gelatin capsule.

Proximal Colonic Delivery Carrier

Eudragit S-100 and dibutyl phthalate are dissolved into 85 parts isopropyl alcohol. Talcum and ferric oxide are subsequently added to the solution followed by homogenization. The resulting suspension is then applied to the hard gelatin capsules of the picosulphate matrix using a perforated pan coater.

Method

A person swallows I hard gelatin capsule and experiences a single episode of laxation 8 hours later without excess laxative-induced cramping.

Example 3

| Picosulphate Matrix | | Proximal Colonic Delivery Carrier | |
|---|---|---|---|
| Component | mg/unit dose | Component | mg/unit dose |
| Picosulphate | 5.0 | Polymethacrylates | 8.7 |
| Polyethylene Glycol 400 | 100.0 | (Eudragit S-100) | |
| | | Dibutyl Phthalate | 1.7 |
| | | Talcum | 2.3 |
| | | Ferric Oxide | 1.3 |

Picosulphate Matrix

Picosulphate is dissolved into polyethylene glycol 400 with mild heat. The resulting solution is then filled into a soft elastic gelatin capsule.

Proximal Colonic Delivery Carrier

Eudragit S-100 and dibutyl phthalate are dissolved into 85 parts isopropyl alcohol. Talcum and ferric oxide are subsequently added to the solution followed by homogenization. The resulting suspension is then applied to the soft elastic gelatin capsules of the picosulphate matrix using a fluid bed coater equipped with a Wurster insert.

Method

A person swallows 1 gelatin capsule and experiences a single episode of laxation 7 hours later without laxative-induced cramping.

Example 4

| Picosulphate Matrix | | Proximal Colonic Delivery Carrier | |
|---|---|---|---|
| Component | mg/unit dose | Component | mg/unit dose |
| Picosulphate | 5.0 | Pulsincap® Capsule | 1 capsule |
| Lactose | 0.2 | Cellulose Acetate | 5.0 |
| Dextrates | 25.0 | Phthalate | |
| | | Castor Oil | 1.2 |

Picosulphate Matrix

Picosulphate is dissolved into Labrafil® 2609 with mild heat.

Proximal Colonic Delivery Carrier

The picosulphate matrix (consisting of a solution of picosulphate in Labrafil® 2609) is filled into a Pulsincap® capsule configured to release its contents approximately six hours following contact with the contents of the gastrointestinal tract. Cellulose acetate cellulose and castor oil are dissolved into 85 parts acetone and the resulting solution is applied to the Pulsincap® capsules of the picosulphate matrix using a perforated pan coater.

Method

A person ingests 1 capsule. Six hours later, the person experiences laxation with no laxative-induced repeat bowel movements.

While particular embodiments of this invention have been described, it will be obvious to those skilled in the art that various changes and modifications of this invention can be made without departing from the spirit and scope of the invention. It is intended to cover, in the appended claims, all such modifications that are within the scope of this invention.

What is claimed is:

1. A pharmaceutical laxative composition in unit dosage form, for peroral administration of picosulphate to a human or other animal subject, comprising:
   (a) from about 0.1 mg to about 10 mg of picosulphate in a rapidly dissolving matrix; and
   (b) a proximal colonic delivery carrier which effects release of said picosulphate substantially near the junction between the small intestine and the colon or within the colon of said subject:

wherein the picosulphate dissolves substantially completely within about 1 minute to about 20 minutes from the matrix once dissolution commences.

2. The composition of claim 1 wherein the picosulphate matrix comprises from about 0.1 mg to about 25 mg of picosulphate.

3. The composition of claim 2 wherein the picosulphate matrix comprises from about 0.5 mg to about 15 mg of picosulphate.

4. The composition of claim 3 wherein the picosulphate matrix is in the form of a compressed tablet.

5. The composition of claim 3 wherein the picosulphate matrix is in the form of a solids-filled hard gelatin capsule.

6. The composition of claim 3 wherein the proximal colonic delivery carrier comprises a pulse capsule.

7. The composition of claim 1 wherein the picosulphate matrix comprises from about 0.5 mg to about 15 mg of picosulphate wherein the picosulphate is in a solid dispersion in a water-soluble carrier selected from the group consisting of polyethylene glycol having a molecular weight greater than about 1000 daltons, poloxamer, citric acid, tartaric acid, dextrose monohydrate, and urea.

8. The composition of claim 1 wherein the picosulphate matrix comprises from about 0.5 mg to about 15 mg of picosulphate in solution in a water-miscible, pharmaceutically-acceptable solvent that is liquid at about 37° C.

9. The composition of claim 8 wherein the picosulphate matrix is encased in a soft gelatin capsule.

10. The composition of claims 1 wherein the proximal colonic delivery carrier comprises a pH-sensitive enteric material which dissolves at a pH of from about 6.5 to about 7.

11. The composition of claim 10 wherein the proximal colonic delivery carrier comprises a pH-sensitive enteric material which dissolves at a pH of about 7.

12. A method for providing laxation for humans and animals in need thereof by peroral administration of the composition of claim 1.

13. A method for providing laxation for humans in need thereof by peroral administration of the composition of claim 10.

* * * * *

UNITED STATES PATENT AND TRADEMARK OFFICE
CERTIFICATE OF CORRECTION

PATENT NO. : 5,631,022
DATED : May 20, 1997
INVENTOR(S) : Kenneth G. Mandel and Paula D. Davis It is certified that error appears in the above-identified patent and that said Letters Patent is hereby corrected as shown below:

Column 5, line 41 "R 6hm" should read --Rohm--.
Column 6, line 12 "5 2,230,442A" should read --2,230,442A--.
Column 7, line 66 " hours" should read --9 hours--.

Signed and Sealed this

Second Day of February, 1999

Attest:

Attesting Officer

Acting Commissioner of Patents and Trademarks